United States Patent [19]

Lider et al.

[11] Patent Number: 5,519,005

[45] Date of Patent: May 21, 1996

[54] METHOD OF INHIBITION OF CELLULAR AND MOLECULAR LEVEL BIOLOGICAL INTERACTIONS UTILIZING NON-PEPTIDIC SURROGATES OF THE ARG-GLY-ASP SEQUENCE

[75] Inventors: Ofer Lider, Rehovot; Noam Greenspoon, Givat Shumel; Rami Hershkoviz, Herzlia; Ronen Alon, Givataim, all of Israel

[73] Assignee: Yeda Research and Development Co. Ltd., Rehovot, Israel

[21] Appl. No.: 251,027

[22] Filed: May 31, 1994

Related U.S. Application Data

[62] Division of Ser. No. 978,582, Nov. 19, 1992, Pat. No. 5,357,667.

[30] Foreign Application Priority Data

| Nov. 22, 1991 | [IL] | Israel | 100130 |
| Jan. 21, 1992 | [IL] | Israel | 100726 |
| Jul. 30, 1992 | [IL] | Israel | 102685 |

[51] Int. Cl.$^6$ ............... A61K 37/00; A61K 37/02; C07C 259/06; C07C 279/04
[52] U.S. Cl. ............... 514/19; 514/20; 514/18; 514/822; 530/322; 562/560
[58] Field of Search ............... 514/18, 19, 20, 514/822; 530/322; 562/560

[56] References Cited

U.S. PATENT DOCUMENTS 5,352,667  10/1994  Lider et al. ............... 514/19

Primary Examiner—John W. Rollins
Assistant Examiner—Jon P. Weber
Attorney, Agent, or Firm—Kohn & Associates

[57] ABSTRACT

A method of inhibition of cellular and molecular level biological interactions which are dependent on RGD interactions is disclosed. The method comprises administering a compound of the formula I $$H_2N-C(=NH)-NH-CH_2-A-CH_2-CO_2H \qquad (I)$$

and pharmaceutically acceptable salts thereof, wherein A is a chain of 9 atoms selected from the group consisting of:

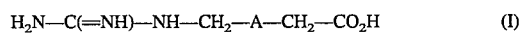
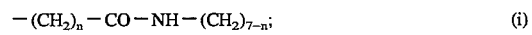
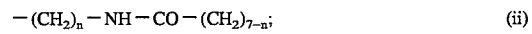
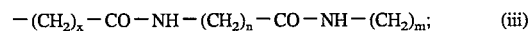
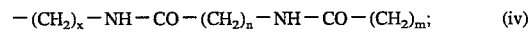
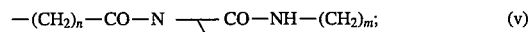

and

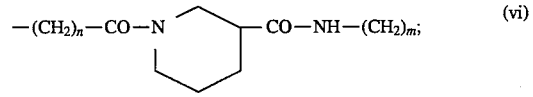
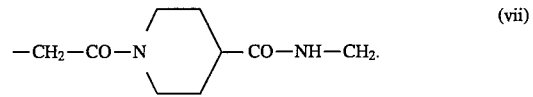

wherein each of x, n and m is at least 1; in chains (i) and (ii) n is at most 6; in chains (iii) and (iv) the sum of x+n+m is 5; and the sum of n+m is 4 in chain (v) and 3 in chain (vi).

11 Claims, 4 Drawing Sheets

| COMPOUND | | NO. OF ATOMS IN THE SPACER |
|---|---|---|
| SF-6,5 |  | 11 |
| AC-15 |  | 11 |
| AC-4 |  | 11 |
| AC-14 |  | 11 |
| SF-6,6 |  | 12 |
| SFN-70 |  | 11 |

NS-8

NS-11

NS-15

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
      ( A ) LENGTH: 3 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Arg  Gly  Asp
   1

( 2 ) INFORMATION FOR SEQ ID NO:2:

( i ) SEQUENCE CHARACTERISTICS:
      ( A ) LENGTH: 3 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Arg  Ala  Asp
   1

( 2 ) INFORMATION FOR SEQ ID NO:3:

( i ) SEQUENCE CHARACTERISTICS:
      ( A ) LENGTH: 3 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Arg  Glu  Asp
   1

( 2 ) INFORMATION FOR SEQ ID NO:4:

( i ) SEQUENCE CHARACTERISTICS:
      ( A ) LENGTH: 3 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Arg  Phe  Asp
   1

( 2 ) INFORMATION FOR SEQ ID NO:5:

( i ) SEQUENCE CHARACTERISTICS:
      ( A ) LENGTH: 3 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:5:

Arg Tyr Asp
1

( 2 ) INFORMATION FOR SEQ ID NO:6:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Asp Gly Arg
1

( 2 ) INFORMATION FOR SEQ ID NO:7:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Arg Gly Glu
1

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Arg Gly Asp Ser
1

( 2 ) INFORMATION FOR SEQ ID NO:9:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Arg Ala Asp Ser
1

( 2 ) INFORMATION FOR SEQ ID NO:10:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Arg Phe Asp Ser
1

( 2 ) INFORMATION FOR SEQ ID NO:11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Arg Tyr Asp Ser
1

( 2 ) INFORMATION FOR SEQ ID NO:12:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Ser Asp Gly Arg
1

( 2 ) INFORMATION FOR SEQ ID NO:13:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

Gly Arg Gly Asp Ser Pro
1               5

( 2 ) INFORMATION FOR SEQ ID NO:14:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

Gly Arg Gly Glu Ser Pro
1               5

( 2 ) INFORMATION FOR SEQ ID NO:15:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear (ii) MOLECULE TYPE: peptide (xi) SEQUENCE DESCRIPTION: SEQ ID NO:15:

Gly Arg Gly Asp Ser
1               5

(2) INFORMATION FOR SEQ ID NO:16:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:16:

Gly Arg Gly Asp Ser Pro Lys
1               5

METHOD OF INHIBITION OF CELLULAR AND MOLECULAR LEVEL BIOLOGICAL INTERACTIONS UTILIZING NON-PEPTIDIC SURROGATES OF THE ARG-GLY-ASP SEQUENCE

This application is a divisional of U.S. Ser. No. 07/978,582, filed Nov. 19, 1992, now U.S. Pat. No. 5,352,667, issued Oct. 4, 1994.

FIELD AND BACKGROUND OF THE INVENTION

The present invention relates to novel non-peptidic compounds having terminal guanidino and carboxyl functional groups, to their preparation and to pharmaceutical compositions comprising them for treatment of several pathological disorders.

The ability of various cell types to adhere to and to interact with other cells or with components of the extracellular matrix (ECM) is essential for maintaining cell functions and tissue integrity via signalling between and within the communicating cells (Springer, 1990; Hynes, 1992; Shimizu et al., 1991). Cellular interactions with soluble or insoluble components of the plasma, the interstitial matrix or the ECM, are carried out primarily via a family of cell-surface receptors designated integrins that are present on most cell types, including lymphocytes, tumor cells and platelets (Ruoslahti, 1991; Hynes, 1992).

The integrins are heterodimeric molecules consisting of an alpha (α) and a beta (β) subunits which are non-covalently linked. Eleven α and six β subunits have been identified. The pairing of α and β subunits exhibits high fidelity in certain tissues and cell types but degenerates in other cases.

The integrins play an important role in integrating the ECM outside the cell with the actin-containing cytoskeleton inside the cell. They are two-headed: the extracellular portion is responsible for the binding of adhesive proteins, in many cases recognizing the ARG-Gly-Asp (RGD; SEQ ID No:1) sequences within these ligands, and the intracellular portion interacts with elements of the cytoskeleton.

The target epitope of several integrin receptors is the RGD sequence, a cell adhesion motif shared by several matrix-associated adhesive glycoproteins, such as fibronectin (FN), vitronectin (VN), fibrinogen, thrombospondin, and von Willebrand factor (Yamada & Kennedy, 1984; Hynes, 1992; Ruoslahti, 1988; D'Souza et al., 1991a).

The best characterized of these proteins is fibronectin, a large and abundant glycoprotein of extracellular matrices and plasma, which serves as a prototype cell adhesion molecule. Fibronectin is a multifunctional protein that supports cell attachment and spreading in eukaryotes and also mediates bacterial cell adhesion. It binds to numerous cell surface and matrix constituents including glycosaminoglycans, heparin, proteoglycans, fibrin and collagen, and triggers a variety of cellular responses (Hynes, 1990).

The tripeptide Arg-Gly-Asp (RGD) was identified as the minimal sequence within the central cell binding domain of fibronectin that mediates cell attachment. The RGD sequence is recognized by several receptors, including the αIIbβ3 (also designated GPIIb-IIIa), α3β1, α5β1 (also designated VLA-3 and VLA-5 integrins, respectively) and most of the αv-containing integrins (Hynes, 1992; Elices et al., 1991; Shimizu et al., 1990). Following cell activation, these receptors mediate RGD-dependent cell-matrix adhesion or cell aggregation (Philips et al., 1991; D'Souza et al., 1991a; Adler et al., 1991). When present in solutions, peptides containing the RGD sequence compete with fibronectin and other RGD-containing matrix proteins for binding to their respective integrin receptors and prevent cell adhesion (Springer, 1990; Ruoslahti and Giancotti, 1989). When immobilized on a surface, short synthetic RGD peptides mimic fibronectin cell-binding properties, but their affinity to their corresponding integrin is about $10^2$–$10^3$ lower than that of the native ligands (Humphries, et al., 1986).

The RGD motif is not restricted to fibronectin and in fact it is present within more than hundred proteins. In some proteins, cell adhesive activity has been ascribed to the RGD sequence, whereas in most others the RGD sequence appears to be functionally silent. It was found to be a common motif in cell adhesion molecules and it plays a crucial role in platelet aggregation, the immune response, in cancer metastasis, cell migration to tissues, infection of microbial pathogens, gastrulation in Xenopus and Drosophila embryos. Several proteins, which were found to have the sequence RGD expressed on their surface, promote cell attachment in vitro for no apparent physiological reason, also indicating the generality of this binding.

The functional activity of RGD peptides was demonstrated with a variety of cell types. It is particularly significant that RGD peptides are capable of inhibiting the binding of fibrinogen and other related proteins to platelets (small enucleated blood cells), and inhibit platelet aggregation, the cell-cell interaction critical for thrombus formation. This observation indicated that RGD peptides could function as antithrombotic agents.

European Patent Application published under No. EP 410539 describes fibrinogen receptor antagonists which are small cyclic hexapeptides containing the RGD sequence and are claimed to be useful in inhibiting platelet aggregation. European Patent Application published under No. EP 406428 describes synthetic cyclic peptides containing the RGD sequence which are cell adhesion inhibitors useful as platelet aggregation inhibitors and tumor metastasis suppressors. European Patent Application published under No. EP 394326 describes synthetic peptides which incorporate the sequence RGD in a conformationally stabilised form and which may be utilized either for inhibiting binding of adhesion proteins, e.g. vitronectin, or for promoting cell adhesion, e.g. in vivo uses such as coating of medical devices, including prostheses and implants, or in vitro uses in coating of substrates such as cell culture substrates. European Patent Application published under No. EP 384362 describes modified peptides useful as inhibitors of protein-platelet adhesion, cell-cell adhesion and platelet aggregation. International Application published under No. WO 9011297 describes adhesion peptides comprising a biologically active site which is a cell attachment promoting binding site containing the RGD sequence, and a hydrophobic attachment domain, useful for facilitating the attachment of the peptide to solid substrates, e.g., in coating of prosthetic devices to be implanted.

The physiological roles of RGD-mediated recognition may extend beyond these biological processes. Pathogenic microorganisms may adhere to RGD-containing ECM glycoproteins. Thus, *Trypanosoma cruzi* adheres to fibronectin and peptides modeled from the fibronectin RGD cell attachment domain were shown to inhibit *T. cruzi* infection (Ouaissi et al., 1986).

Interestingly, several non-ECM related proteins contain the RGD or RGD-like molecules. Among these, the RGD sequence is also found in the transactivation (tat) factor of human immunodeficiency virus type-I (HIV-1). The protein which regulates the viral replication also induces other manifestations of the disease, e.g., Kaposi sarcoma. Soluble tat was shown to bind to several integrins in an RGD-dependent manner (Vogel et al. 1992).

Peptides containing Arg-Ala-Asp (RAD; SEQ ID No:2), Arg-Glu-Asp (RED; SEQ ID No:3), Arg-Phe-Asp (RFD; SEQ ID No:4) and Arg-Tyr-Asp (RYD; SEQ ID No:5) sequences were postulated to interfere with immune functions unrelated to integrins. The Arg-Ala-Asp-Ser (RADS; SEQ ID No:9), Arg-Phe-Asp-Ser (RFDS; SEQ ID No:10) and Arg-Tyr-Asp-Ser (RYDS; SEQ ID No:11) sequences have been postulated to constitute functional adhesiotopes of the CD4 or MHC-I and II molecules, respectively (Mazerolles et al., 1990). Human HLA-DR antigen, present on antigen presenting cells, contains the sequence RYDS and is recognized by the T-cell CD4 antigen. Interference with the CD4-HLA-DR interaction might result in incomplete T cell activation.

Synthetic peptides derived from the human major histocompatibility complex class II antigens (MHC-II) containing the peptide RFDS, and a peptide derived from the immunoglobulin-like amino-terminal domain of the T cell CD4 molecules containing the RADS peptide, were shown to exhibit specific inhibitory effect on antigen-induced HLA class-II-restricted T cell proliferative responses and antibody synthesis (Mazerolles et al, 1988).

The RYDS sequence-has been shown to mimic the RGD cell binding domain of fibrinogen. RYD sequence is comprised as essential part of a CDR-3 (complementarity-determining region) of a monoclonal antibody specific for the binding site of the platelet integrin GPIIb-IIIa, specific for FN, fibrinogen, vitronectin etc. A 12-mer peptide derived from this CDR-3, containing the RYDS site, inhibited RGD-dependent fibrinogen binding to its GPIIb-IIIa receptor (Taub et al., 1989). Streptavidin RYD-sequence has also been shown to mimic the RGD sequence and mediate RGD-dependent cell binding and adhesion of the protein (Alon et al., 1990). Recently, REDV sequence of the alternatively spliced cell-binding domain of FN has been shown to be involved in FN-binding to its non-RGD dependent integrin receptor, α4β1 (Mould et al., 1991).

Moreover, the inverted peptide Ser-Asp-Gly-Arg (SDGR; SEQ ID No:12) containing the Asp-Gly-Arg (DGR; SEQ ID No:6) sequence was shown to inhibit spreading of BHK cells and chick embryo fibroblasts on vitronectin-coated substrates and on fibronectin-coated substrates. DGR-containing sequences have been suggested to comprise part of the ligand-binding pocket in integrins, implicated in RGD recognition. At any rate, they may interact with RGD-sequences on adhesive proteins and block or inhibit their interactions with integrins (Yamada and Kennedy, 1987).

The use of peptidic RGD analogues presents several drawbacks, mainly the cleavage of the peptidic bond by proteolytic enzymes in vivo. It would therefore be of great advantage to derive functional mimetics resistant to proteolytic digestion to be used as useful tools for interfering with biologic interactions dependent on RGD recognition, such as integrin-mediated cell functions.

SUMMARY OF THE INVENTION

It has now been found according to the present invention that certain non-peptidic compounds comprising a guanidino and a carboxyl terminal groups with a spacer sequence of 11 atoms between them, are effective inhibitors of cellular or molecular interactions which depend on RXD or DGR recognition, wherein X is G (gly), E (glu), Y (tyr), A (ala) or F (phe). These RXD and DGR analogues are herein referred to as "RXD surrogates".

The present invention thus relates to non-peptidic compounds having no sequence of natural α-amino acids and comprising a guanidino and a carboxyl terminal functional groups spaced by a sequence of 11 atoms, at least 5 of which are carbon atoms, and to salts thereof, which are capable of inhibiting cell adhesion.

In one embodiment, the compounds of the invention correspond to the general formula

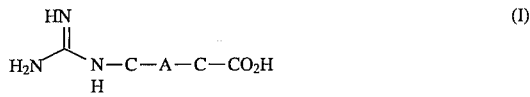

wherein A is a chain of 9 atoms, at least 3 of which are carbon atoms, the remainder being heteroatoms, such as nitrogen, oxygen and/or sulfur atoms. The 9-atom chain A may be saturated or unsaturated, substituted or unsubstituted, and may include carbocyclic or heterocyclic radicals comprising 1 or more atoms of the A chain as members of the ring.

The invention further relates to methods for the preparation of the non-peptidic compounds of the invention.

The RXD surrogates of the invention have various applications related to their inhibition of biological interactions dependent on RXD and DGR recognition, particularly integrin-mediated RGD-dependent interactions. Thus the invention also relates to pharmaceutical compositions comprising the RXD surrogates for the treatment of several disorders, such as thrombosis, metastasis, autoimmune diseases and other immune responses such as allergy, graft versus host and host versus graft reactions, and inhibition of scar-tissue formation.

DETAILED DESCRIPTION OF THE INVENTION

Figure 1:
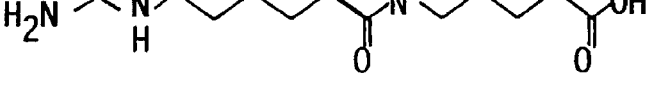
FIG. 1 depicts the chemical structure of compounds according to the invention identified as SF-6,5, AC-15, AC-4 and AC-14, and compounds used for comparison identified as SF-6,6 and SFN-70.
Figure 1:
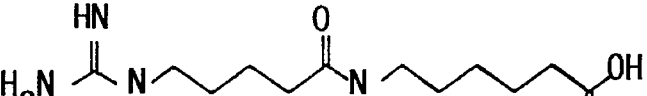
Figure 1:
Figure 1:
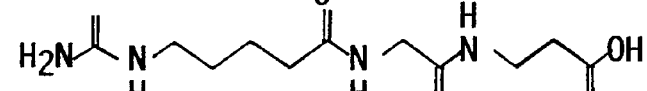
Figure 1:
Figure 1:
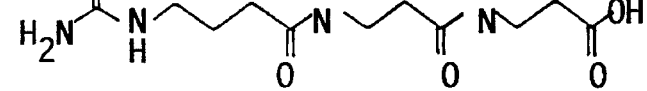

In designing the non-peptidic ARG-Gly-Asp (RGD; SEQ ID No:1) surrogates according to the present invention, it was taken into consideration that the major contribution to the binding affinity of the known RGD-containing peptides to their putative sites on integrins depends on the guanidinium and carboxylate groups of the Arg and Asp moieties, respectively, based on structure-function studies demonstrating the indispensable role of the Arg and Asp residues for integrin recognition (D'Souza et al., 1991b), and the fact that an adequate atomic spacing between these two functional groups seems to be obligatory, based on the evidence that ARG-Gly-Glu (RGE; SEQ ID No:7)-containing peptides lack integrin specificity and do not bind integrins or bind integrins with much lower affinity than the RGD ligands (D'Souza et al. 1991b; Shimizu et al., 1990). Furthermore, it was considered that even a relatively flexible chain molecule with appropriate functionalities at the required atomic distances can exhibit functional effects resembling those of RGD-containing peptides.

As used herein the term "RXD surrogates" refers to novel non-peptidic compounds having no sequence of natural α-amino acid residues and comprising a guanidino and a carboxyl terminal groups spaced by a chain of 11 atoms, at least 5 of which are carbon atoms, and the remainder are carbon or heteroatoms, such as nitrogen, oxygen and/or sulfur atoms, as well as to salts thereof.

The two carbon atoms adjacent to the terminal functional guanidino and carboxy groups are preferably not substituted as shown in Formula I herein. The remaining 9-atom chain may be saturated or unsaturated, substituted or unsubstituted.

The substituents in the spacer chain include, but are not limited to, radicals such as halogen, amino, oxo, thioxo, imino, hydrocarbyl, heterocyclic, carboxyl and thiocarboxyl and esters thereof, carboxamido, thiocarboxamido, carbamoyl, thiocarbamoyl, hydroxy, and ethers and esters thereof, mercapto and ethers and esters thereof. All the substituents having a hydrogen atom may be further substituted, e.g. by a hydrocarbyl or heterocyclic radical. The esters and ethers herein comprise aliphatic, aromatic and heterocyclic residues, preferably hydrocarbyl and heterocyclic residues that may be further substituted as indicated above for the spacer chain. Esters of hydroxyl groups may be formed also with inorganic acids, e.g., phosphoric acid. In addition, one or more atoms of the spacer chain may form part of a carbocyclic or heterocyclic ring having at least 3 members.

The term "hydrocarbyl" herein refers to $C_1$–$C_{15}$ saturated and unsaturated radicals selected from aliphatic, cycloaliphatic and aryl radicals, such as alkyl, alkenyl, cycloalkyl and aryl radicals. Preferred hydrocarbyl radicals are $C_1$–$C_8$, more preferably $C_1$–$C_4$ alkyl radicals, and phenyl.

The term "heterocyclic" herein refers to saturated and unsaturated 3–8, preferably 5–7 membered heterocyclic radicals containing one or more N, O and/or S atoms, such as piperidyl and pyridyl.

For use in therapeutics, the compound should be soluble in water and any substituent resulting in a soluble compound is encompassed by the invention. Examples of such substituents are oxo groups, thus forming —CO—NH- or —NH—CO-groups within the chain, and carboxy and/or amino groups.

A preferred series of compounds according to the invention includes compounds having one or more —CO—NH-residues and may be represented by the following formulas:

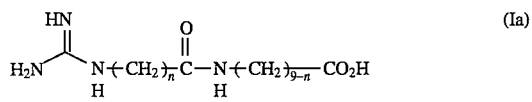

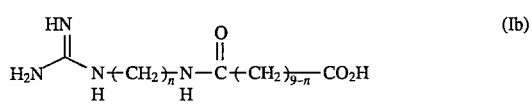

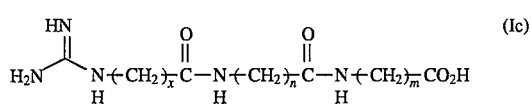

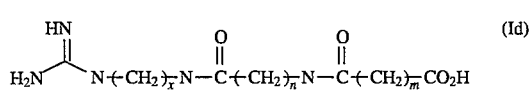

wherein in formulas Ia and Ib n is at least 1 and at most 8, and in formulas Ic and Id each of x, n and m is at least 1 and the sum of x+m+n is 7. Illustrative compounds of this series are the compounds herein designated SF-6,5 and AC-15, whose formulas are depicted in FIG. 1, and are compounds of formula Ia wherein n is 5 and 4, respectively, and the compounds herein designated AC-4 and AC-14, whose formulas are depicted in FIG. 1 and are compounds of formula Ic wherein x is 4, n is 1 and m is 2 or x is 3 and each of n and m is 2, respectively.

Other compounds according to the invention are illustrated by the following formulas:

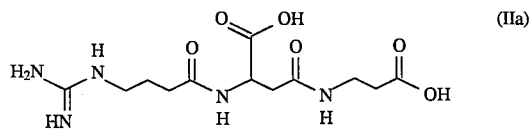

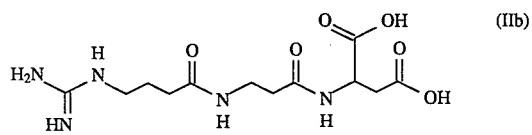

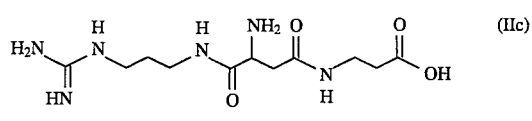

Another series of preferred compounds according to the invention comprises compounds having one or more —CO—NH-residues and a carbocyclic, particularly a phenyl ring, or heterocyclic, particularly a piperidine ring, as part of the A chain. Whenever one or more atoms of the A chain form part of such a ring, they are comprised according to the invention within the shortest chain of the ring between atoms of the open chain. These compounds may be represented by the following formulas:

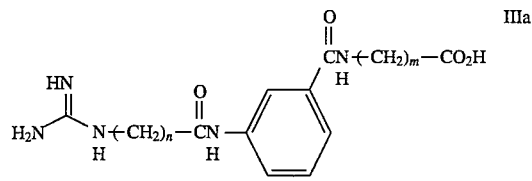

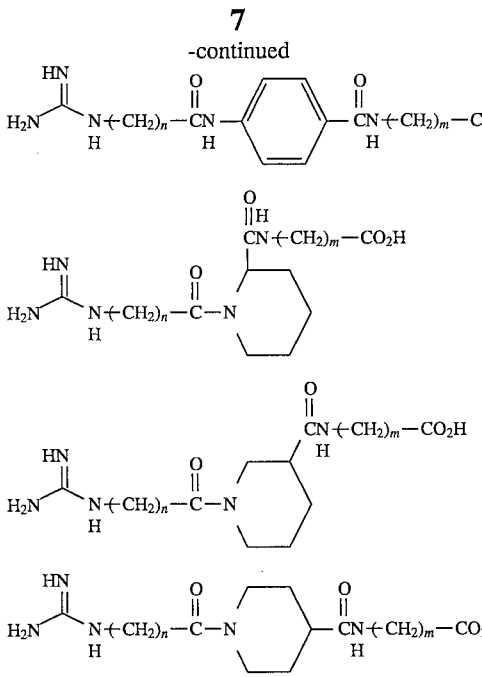

wherein each of n and m is at least 1 and the sum of n+m is 6 in formula IIIc, 5 in formula IIId, 4 in formulas IIIa and IIIe and 3 in formula IIIb. Illustrative compounds of this series are compounds NS-8, NS-11 and NS-15 depicted in FIG. 2, which are compounds of formula IIIc (n=4, m=2), IIId (n=3, m=2) and IIIa (n=m=2), respectively.

Another series of preferred compounds are those of the following formulas:

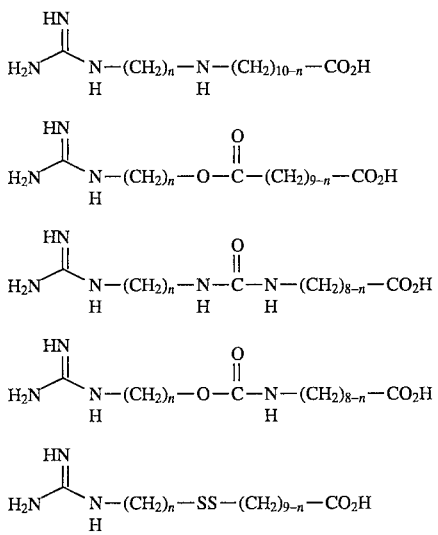

wherein n is at least 1 and at most 7 in formulas IVc and IVd, 8 in formulas IVb and IVe, and 9 in formula IVa.

The invention further comprises salts of the surrogates of the invention derived from organic or inorganic bases.

The compounds of formula Ia are prepared by a process comprising of the following steps:

(a) coupling an N— protected aminocarboxylic acid of the formula $ZNH—(CH_2)_n—COOH$ (wherein Z is a protecting group, such as N-t-butyloxycarbonyl, herein N-t-Boc) with an alkyl ester of an aminocarboxylic acid of the formula $H_2N—(CH_2)_{9-n}—COOR$, wherein R is lower alkyl, using standard procedure, for example, with 1,3-dicyclohexylcarbodiimide and 1-hydroxybenzotriazole or N-hydroxysuccinimide;

(b) removing the protecting group from the obtained compound of the formula $ZNH—(CH_2)_n—CO—NH—(CH_2)_{9-n}—COOR$, for example, with trifluoroacetic acid, resulting in a compound of the formula $H_2N—(CH_2)_n—CO—NH—(CH_2)_{9-n}—COOR$; and (c) converting the free amino group to a guanidino group, for example, by reaction with 3,5-dimethylpyrazole 1-carboxamidine nitrate, with concomitant removal of the ester group R.

According to the above process, the compounds SF-6,5 and AC-15 were prepared by coupling methyl 6-aminohexanoate with N-t-butyloxycarbonyl-5-aminopentanoic acid, or methyl 5-aminopentanoate with N-t-butyloxycarbonyl-6-aminohexanoic acid, respectively, using 1,3-dicyclohexylcarbodiimide and 1-hydroxybenzotriazole in dichloromethane. The butyloxycarbonyl protecting group was then removed by 50% trifluoroacetic acid in dichloromethane, and the amine was converted to guanidine using 3,5-dimethylpyrazole 1-carboxamidine nitrate at pH 9.5. The methyl group was removed under the reaction conditions.

Compounds of formula Ic are prepared by stepwise synthesis on a Merrifield resin according to standard procedure (Barany and Merrifield, 1980), Thus an N-t-Boc-omega-amino acid is prepared and coupled to a chloromethylated polystyrene 1% divinyl benzene by the cesium salt method. Coupling on the polymer may be carried out manually with 2 fold excess of the N-t-Boc-omega-amino acid with an equimolar mixture of N,N'-dicyclohexylcarbodiimide and 1-hydroxybenzotriazole as reagents. Deprotection by 50% trifluoroacetic acid in methylene chloride and coupling to the next N-t-Boc-omega-amino acid under the same conditions yields the final product coupled to the polymer. Deprotection and cleavage from the resin is achieved by treatment with anhydrous HF. The crude product is extracted in 50% acetic acid and lyophilized. Conversion of the amino to the guanidino group is carried out as described above for the preparation of compound Ia. The final product is purified by reverse phase chromatography followed by preparative HPLC purification.

Compounds of formula Ib are prepared by a stepwise synthesis comprising coupling of a monoprotected diamine of the formula $ZNH—(CH_2)_n—NH_2$ with a monoalkyl ester of a dicarboxylic acid of the formula $HOOC—(CH_2)_{9-n}—COOR$, wherein R is lower alkyl, and removal of the protecting group and conversion of the amino to the guanidino group, as described above in steps (b) and (c) for the preparation of compounds of formula Ia. For example, when n is 3, N-monobenzyloxycarbonyl-propanediamine is coupled with the monomethyl ester of suberic acid.

Compounds of formula Id are prepared by first coupling an aminocarboxylic acid of the formula $HOOC—(CH_2)_n—NH_2$ with a monoester of a dicarboxylic acid of the formula $HOOC—(CH_2)_m—COOR$, wherein R is lower alkyl, followed by further coupling with a monoprotected diamine of the formula $ZNH—(CH_2)_x—NH_2$, removal of the protecting group and conversion of the amino to guanidino group as described above. When x is 3 and n=m=2, β-alanine is coupled with monomethylsuccinate and the resulting compound is coupled with N-monobenzyloxycarbonyl-propanediamine.

Compounds substituted by amino or carboxyl groups, such as those of formulas IIa, IIb and IIc above, are prepared by stepwise synthesis on a Merrifield resin, using the appropriate substituted aminocarboxylic acid and/or monoprotected diamine (comp. IIc).

Compounds of the formulas IIIa–e are prepared by stepwise synthesis on a Merrifield resin according to standard procedure as described above for preparation of compounds of formula Ic.

Compounds of formula IVa are prepared by a process comprising coupling of a monoprotected diamine of the formula ZNH—$(CH_2)_n$—$NH_2$ (wherein Z is a protecting group, such as N-t-Boc or benzyloxycarbonyl) with an alkyl ester of an omega-bromocarboxylic acid of the formula Br—$(CH_2)_{10-n}$—COOR wherein R is lower alkyl, using standard procedure, for example, dimethyl formamide as solvent and triethyl amine as base. Removal of the protecting group and conversion of the primary amine to the guanidino group is carried out as decribed above for the preparation of compounds of the formula Ia. Thus, to prepare a compound wherein n is 5, N-monobenzyloxycarbonyl-pentanediamine is coupled with the methyl ester of 5-bromovaleric acid.

Compounds of formula IVb are prepared by a process comprising coupling of an N-protected amino alcohol of the formula ZNH—$(CH_2)_n$—OH with a monoester of a dicarboxylic acid of the formula HOOC—$(CH_2)_{9-n}$—COOR using 1,3-dicyclohexylcarbodiimide as the coupling agent. Removal of the protecting group and conversion of the primary amine to the guanidino group is carried out as described above for the preparation of compounds of the formula Ia. Thus to prepare a compound wherein n is 5, N-t-butyloxycarbonylamino pentanol is coupled with monomethyl adipate.

Compounds of formula IVc are prepared by a process comprising reaction of an omega-bromocarboxylic acid ester of the formula Br—$(CH_2)_{8-n}$—COOR and sodium cyanate, thus forming an omega-isocyanatocarboxylic acid alkyl ester of the formula OCN—$(CH_2)_{8-n}$—COOR acid. Further reaction with a monoprotected diamine of the formula ZNH—$(CH_2)_n$—$NH_2$ produces the protected urea of the formula ZNH—$(CH_2)_n$— HNCONH$(CH_2)_{8-n}$—COOR. Removal of the protecting group and conversion of the primary amine to the guanidino group is carried out as described above for the preparation of compounds of the formula Ia. Thus, to prepare a compound wherein n is 3, 5-bromovaleric acid methyl ester is converted to 5-isocyanatovaleric acid methyl ester which is then reacted with N-monobenzyloxycarbonyl-propanediamine.

Compounds of formula IVd are prepared by reacting an omega-isocyanatocarboxylic acid alkyl ester of the formula OCN—$(CH_2)_{8-n}$—COOR, prepared as above, with an N-protected amino alcohol of the formula ZNH—$(CH_2)_n$—OH to form the protected carbamate of the formula ZNH—$(CH_2)_n$— OCONH$(CH_2)_{8-n}$—COOR. Removal of the protecting group and conversion of the primary amine to the guanidino group is carried out as described above for the preparation of compounds of the formula Ia. For example, to prepare a compound wherein n is 3, 5-isocyanatovaleric acid methyl ester is reacted with 3-N-t-butyloxycarbonylamino propanol.

Compounds of formula IVe are prepared by a process comprising the following steps: (a) an omega-acetylthiocarboxylic acid alkyl ester of the formula $CH_3COS$—$(CH_2)_{9-n}$—COOR is prepared by reaction of an omegabromocarboxylic acid alkyl ester of the formula Br—$(CH_2)_{9-n}$—COOR with sodium thioacetate, (b) an N-protected amino alcohol of the formula ZNH—$(CH_2)_n$—OH is converted first to its tosylate by reaction with p-toluene sulfonyl chloride in pyridine and then by reaction with sodium thioacetate, to the thioacetate of the formula ZNH—$(CH_2)_n$—$SCOCH_3$, (c) the acetate groups of the compounds prepared in steps (a) and (b) are removed under basic conditions, e.g., sodium carbonate, producing the corresponding thiol compounds; and (d) the asymmetrical disulfide of the formula ZNH—$(CH_2)_n$ SS$(CH_2)_{9-n}$—COOR is then formed by reaction of the two thiols of step (c) using diethyl azadicarboxylate as oxidation agent. For example, to prepare a compound wherein n is 4, 5-bromovaleric acid methyl ester is converted to the protected thiol by reaction with sodium thioacetate, and N-t-butyloxycarbonyl-4-aminobutanol is converted to the corresponding tosylate followed by substitution, with sodium thioacetate. The acetate groups are then removed under basic conditions and the resulting N-t-butyloxycarbonyl-4-aminobutanethiol is added to a solution containing the resulting 5-mercaptovaleric acid methyl ester and diethyl azadicarboxylate.

All the final compounds were purified on preparative RP-18 columns and were judged pure by thin layer chromatography (single spot) and $^1$H NMR spectroscopy. Compounds were characterized by $^1$H NMR and FAB MS spectroscopy which were consistent with the assigned structures.

The RXD surrogates of the invention can inhibit biological interactions which are dependent on RXD recognition. Examples of versatile recognition processes mediated by the RXD pattern encompassed by the present invention include, but are not limited to, cellular and molecular interactions involving the ARG-Gly-Asp (RGD; SEQ ID No:1), Arg-Tyr-Asp (RYD; SEQ ID No:5), Arg-Glu-Asp (RED; SEQ ID No:3), Arg-Ala-Asp (RAD; SEQ ID No:2), Arg-Phe-Asp (RFD; SEQ ID No:4) and Asp-Gly-Arg (DGR; SEQ ID No:6) sequences, in particular integrin-mediated RGD-dependent interactions.

The non-peptidic RXD surrogates of the invention inhibit cell adhesion. As used herein the term "cell adhesion" encompasses any of the following interactions: (a) cell-cell adhesion, illustrated by platelet aggregation; (b) cell adhesion to glycoproteins of the serum or of the ECM, illustrated by adhesion of lymphocytes and metastatic tumor cells to RGD-containing glycoproteins of ECM; (c) pathogenic organisms adherence to RGD-containing glycoproteins of ECM, illustrated by adhesion of *Trypanosoma cruzi* to fibronectin; and (d) cell adhesion to RGD-containing non-ECM proteins, illustrated by adhesion of lymphocytes to the tat factor of HIV-1.

The surrogates of the invention are capable of inhibiting platelet aggregation. The interaction of lymphocytes and tumor cells with FN present in the interstitial matrix and on cell surfaces have been postulated to play a major role in cell adhesion and migration. In view of the ability of RGD surrogates to interfere with platelet aggregation, it was tested whether they could also competitively inhibit T lymphocytes and tumor cells binding to FN or VN; such inhibition has been shown to be strongly associated with the RGD sequence on both of those adhesive proteins (van Seventer et al, 1991; Shimizu et al, 1990; Adler et al, 1991; Ruoslahti et al, 1989). The answer was positive and the results are shown in Tables 1A and 1B hereinbelow.

As inhibitors of cell adhesion the compounds of the invention can inhibit adhesion of cancer cells to fibronectin and vitronectin, and thus can prevent metastasis. They also block lymphocyte migration to tissues and thus inhibit several immune disorders, such as allergy, which depends on immune cells. They also inhibit platelet aggregation and thus can be used in the prevention and/or treatment of platelet thrombosis, thromboembolism, reocclusion after angioplasty of coronary and other arteries and myocardial infarction. In addition, the surrogates inhibit key lymphocyte interaction with certain antigen-presenting cells and thus inhibit T cell activation, being useful in the treatment of autoimmune diseases. Through competition with fibronectin recognition by fibroblasts implicated in the fibrosis process, the surrogates inhibit scar tissue formation at a very early stage, being useful in wound healing process.

Thus in one preferred embodiment, the compounds of the invention are RGD surrogates and will inhibit both cellular and molecular interactions which are RGD dependent. In this respect, the compounds are useful in the treatment of a series of disorders, including thrombosis, autoimmune diseases, metastasis, immune disorders such as allergy, graft versus host and host versus graft reactions, and in wound healing in the inhibition of scar formation.

The compounds of the invention can be administered to patients by any suitable route including oral and parenteral routes, e.g., intravenous, subcutaneous or intramuscular injection. An effective but essentially non-toxic quantity of the compound will be employed in the treatment. Effective amounts may be within the range of 0.01 to 1 mg/kg, preferably 0.5 mg/kg on a regimen in single or several daily doses.

The invention further provides a pharmaceutical composition comprising as active ingredient a surrogate according to the invention and a pharmaceutically acceptable carrier. The compositions may be in the form of tablet, capsule, solution or suspension containing from about 0.7 to 70 mg per unit of dosage of an active compound of the invention or mixtures thereof. The compounds may be compounded in conventional manner with a physiologically acceptable vehicle or carrier, excipient binder, preservative, stabilizer, etc. For example, injections for intravenous administration may be prepared in saline, at a pH level of e.g. 7.4, suitable for achieving inhibition of platelet aggregation.

In another embodiment the RGD surrogates of the invention can be used as promoters of cell adhesion to a surface, for example, in vivo uses such as coating of medical devices, including prostheses or implants, e.g., vascular implants thus facilitating the attachment of cells thereto. They may also be used in vitro for coating of substrates, e.g. cell culture substrates to promote cell adhesion.

The following examples are intended to illustrate, by way of example, the principles of the invention, without limiting it thereto.

EXAMPLES

Example 1. Preparation of 6-aza-7-oxo-12-guanidino-dodecanoic acid [SF-6,5]

1.1 Preparation of N-t-Boc-6-aminohexanoic acid [compound 2]

Di-t-butylpyrocarbonate (8.31 g, 38 mmol) was added to a solution of 6-aminohexanoic acid [compound 1] (5 g, 38 mmol) and sodium hydroxide (38 ml, 2N solution) in dioxane (30 ml).

The solution was stirred at room temperature for 4 hours, then it was acidified with 2N HCl and poured into ether (100 ml). The phases were separated, the ether layer was dried and removed under reduced pressure, whereupon compound [2] was obtained and used in the next step without further purification.

1.2 Preparation of methyl 5-aminopentanoate [compound 4]

5-Aminopentanoic acid [compound 3] (5 g, 41 mmol) was added to a saturated HCl solution in dry methanol (100 ml). The solution was left for 3 h at room temperature and the methanol was removed under reduced pressure. The residue was redissolved in a minimum amount of methanol and precipitated by addition of ether, whereupon the white crystaline compound [4] was obtained, filtered, washed with ether, dried in vacuo and used in the next step without further purification.

1.3 Coupling of compounds [2] and [4] by the active ester method.

An active ester of compound [2] was generated by addition of 1,3-dicyclohexylcarbodiimide (DCC) (490 mg, 2.37 mmol) to a solution containing compound [2] (500 mg, 2.16 mmol) and N-hydroxysuccinimide (273 mg, 2.37 mmol) in $CH_2Cl_2$/THF 1:1 (v/v) solution (7 ml) and left overnight at room temperature. The resulting active ester solution was filtered to remove dicyclohexylurea (DCU) generated in the reaction and washed with dry $CH_2Cl_2$. A solution of compound [4] containing triethyl amine (to neutralize the amine hydrochloride) in DMF (5 ml) was then added to the active ester of compound [2] solution. After 5 h, the solution was poured into 5% aqueous sodium bicarbonate (100 ml) and the product was extracted with ether. The ether was dried over $Na_2SO_4$ and removed under reduced pressure, whereupon the crude product [5] was obtained pure enough for the next step.

1.4 Removal of the N-t-Boc protecting group

The crude product [5] was dissolved in $CH_2Cl_2$:TFA (trifluoroacetic acid) 1:1 v/v at 0° C. After 30 min, the solution was allowed to warm to room temperature for 30 min. The solvents were removed under reduced pressure, the crude product was dissolved in water and washed with ether. The water was removed under reduced pressure, whereupon the crude product with a free amino group was obtained and used in the next step without further purification.

1.5 Preparation of the compound SF-6,5

3,5,Dimethylpyrazole 1-carboxamidine nitrate (175 mg, 0.87 mmol) was added to a solution containing the deprotected amine (200 g, 0.87 mmol) obtained in step 1.4 in ethanol (5 ml), and NaOH (2N) was added to the solution to bring the pH to 9.5. The solution was stirred overnight at 50° C., the solvent was removed under reduced pressure and the crude product SF-6,5 was purified by reverse phase chromatography, followed by HPLC using RP-18 column. Purity was checked by NMR.

NMR: 3.18(t, J=6.54 Hz, 2 H); 3.16(t, J=6.90 Hz, 2 H); 2.39(t, J=7.19, 2 H); 2.23(t, J=7.21 Hz, 2 H); 1.64–1.49(M, 8 H); 1.33 (tt, 2 H). FAB-MS (m/e): 273.3 M+1).

Example 2. Preparation of 7-aza-8-oxo-12-guanidino-dodecanoic acid [AC-15]

The compound AC-15 was prepared similarly to compound SF-6,5 as described in Example 1, but using as starting materials methyl 5-aminopentanoate and N-t-butyloxycarbonyl 6-aminohexanoic acid. Purity was checked by NMR.

NMR: 2.98(t, J=6.45 Hz, 2 H); 2.97(t, J=6.69 Hz, 2 H); 2.06(t, J=6.79 Hz, 2 H); 1.97(t, J=7.38 Hz, 2 H); 1.49–1, 24(m, 8 H); 1.16–1.05(tt,2 H). FAB-MS: (m/e): 273.3 (M+1).

Example 3. Preparation of compound SF-6,6

This compound has an extra methylene group in the spacer chain and was used for comparison with the compounds of the invention. It was prepared similarly to compound SF-6,5 as described in Example 1, but using as starting compounds N-t-Boc- 6-aminohexanoic acid and methyl 6-aminohexanoate.

NMR: 3.03(t, J=6.75 Hz 2 H); 3.02(t, J=6.96 Hz, 2 H); 2.23(t, J=7.38, 2 H); 2.09(t, J=7.28 Hz, 2 H); 1.46(M, 6 H); 1.37(Q, 2 H); 119(tt,4 H). FAB-MS (m/e): 287.3(M+1).

Example 4. Preparation of compound SFN-70

This compound has a similar structure to compound SF-6,5, but instead of a terminal guanidino group it has a primary amino group. It was prepared by hydrolysis of the appropriate ester from Example 1.4 in aqueous base, and used for comparison with the compounds of the invention.

Example 5. Preparation of 4,8-diaza-5,9-dioxo-12-guanidino-dodecanoic acid [AC-14]

N-t-Boc-β-alanine was prepared as described in Example 1 for the 6-aminohexanoic acid and was coupled to a chloromethylated polystyrene 1% divinyl benzene by the cesium salt method. Thus t-Boc-β-alanine (1.73 g, 0.01 mol) was dissolved in water (10 ml) and the pH was adjusted to 7.0 by adding a solution of 1M $Cs_2CO_3$. The solvent was removed under reduced pressure and the residue was dried in vacuo over $P_2O_5$. The dry salt was dissolved in DMF and was added to the polymer. The mixture was kept at 50° for 12 h with occasional shaking. The solvent was filtered off and the polymer was washed successively with DMF, DMF-:water 9:1 mixture and ethanol and was dried in vacuum. Coupling on the polymer was carried out manually. Thus after deprotection with 50% trifluoroacetic acid in methylene chloride, coupling to N-t-Boc-β-alanine was performed with 2 fold excess of the protected amino acids with an equimolar mixture of 1,3-dicyclohexyl-carbodiimide and 1-hydroxybenzotriazole as reagents. Deprotection and coupling to N-t-Boc-gamma-aminobutyric acid under the same conditions gave the final product coupled to the polymer. Deprotection and cleavage from resin was achieved by treatment with anhydrous HF.

The crude product was extracted in 50% acetic acid and lyophilized. Conversion of the amino to the guanidino group was carried out as described for the preparation of compound SF-6,5 in Example 1. The final product was purified by reverse phase chromatography followed by preparative HPLC purification.

AC-14, NMR; 3.58(t, J=6.41 Hz, 2 h); 3.52(t, J=6.74 Hz, 2 H); 2.56(t, J=6.42 Hz, 2 H); 2.53(t, J=6.72 Hz, 2 H); 2.44(t, J=7.25 Hz, 2 H); 2.00 (Q, 2 H). FAB-MS: (m/e): 288.3 (M+1).

Example 6. Preparation of 4,7-diaza-5,8-dioxo-12-guanidino-dodecanoic acid [compound AC-4]

This compound corresponds to the formula (Ic) where x is 4, n is 1 and m is 2. It was prepared similarly to compound AC-14 as described in Example 5.

NMR; 3.70(S, 2 H); 3.31(t, J=6.3 Hz, 2 H); 3.04(t, J=6.6 Hz, 2 H); 2.44(t, J=6.4 Hz, 2 H); 2.19(t, J=6.7 Hz, 2 H); 1.46(M, 4 H). FAB-MS: (m/e): 288.3 (M+1).

Example 7. Preparation of 4,8-diaza-5,9-dioxo-7-carboxy-12-guanidino-dodecanoic acid [compound IIa]

Compound [IIa] was prepared on a Merrifield resin starting with N-t-Boc-β-alanine coupled to the polymer as in Example 5. Coupling on-the polymer was carried out manually as in Example 5, first coupling to α-benzyl N-t-Boc-aspartic acid followed by coupling to N-t-Boc-gamma-aminobutyric acid. Deprotection, cleavage from the resin and conversion of the amino to the guanidino group were carried out as in Example 5.

Example 8. Preparation of 4,8-diaza-5,9-dioxo-3-carboxy-12-guanidino-dodecanoic acid [compound IIb]

For preparation of the compound [IIb], α-benzyl N-t-Boc-aspartic acid was coupled to the Merrifield resin by the same method described in Example 5. Stepwise synthesis by addition of N-t-Boc-β-alanine followed by coupling to N-t-Boc-gamma-aminobutyric acid produced after deprotection, cleavage, conversion of the amino to the guanidino group and reverse phase chromatography, the compound [IIb].

Example 9. Preparation of 4,9-diaza-5,8-dioxo-7-amino-12-guanidino-dodecanoic acid [compound IIc]

Compound IIc was prepared by stepwise synthesis in solution starting with benzyl β-alanine using the active ester method as in the Merrifield method. Thus benzyl β-alanine was coupled to α-benzyl N-t-Boc-aspartic acid and the product was deprotected in $TFA:CH_2Cl_2$ 1:1 as in Example 1.4. It was then coupled to monobenzyloxycarbonyl 1,3-propanediamine. Deprotection, followed by conversion of the amino to the guanidino group as described in Example 1.5, gave compound IIc which was purified by reverse phase chromatography.

Example 10. Preparation of 9-aza-8-oxo-12-guanidino-dodecanoic acid [compound Ib, wherein n=3]

10.1 The diprotected diamine $H_2N-(CH_2)_3-NH_z$ was prepared by adding benzyloxycarbonylchloride (1.2 mole) with 2 equivalents of 1N NaOH to a solution of the diamine (1 mole) in water (500 ml). The product was washed with water and hexane, dried over $P_2O_5$, and recrystallized from ethanol.

10.2 The monoprotected diamine was prepared by heating under reflux a solution of (0.06 mole) of the diprotected diamine in glacial acetic acid (100 ml) and concentrated HCl (10 ml, 0.12 mole) for 1 h and allowing to stand at room temperature overnight. The dihydrochloride of the diamine was crystallized and was filtered. The monobenzyloxycarbonylpropanediamine was precipitated from the filtrate by the addition of ether. It was filtered, washed with ether and dried and was found to be pure enough for use in the next step.

10.3 1,3-Dicyclohexylcarbodiimide (490 mg), 2.37 mmol) was added to a solution containing monomethyl suberate (2.16 mmol) and N-hydroxysuccinimide (2.37 mmol) in $CH_2Cl_2/THF$ 1:1 (v/v) solution (7 ml). The reaction was left overnight at room temperature, the solution was filtered to remove DCU and washed with dry $CH_2Cl_2$. Monobenzyloxycarbonylpropanediamine of step 10.2 in solution containing triethyl amine (to neutralize the amine hydrochloride) in DMF (5 ml) was then added to the active ester solution. After 5 h, the solution was poured into 5% aqueous sodium bicarbonate (100 ml) and the product was extracted with ether. The ether was dried over $Na_2SO_4$ and was removed under reduced pressure. The crude coupling product was pure enough for the next step.

10.4 The benzyloxycarbonyl protecting group was removed and the crude amine was converted to the guanidine (the methyl ester group was cleaved under the reation conditions), as described in previous examples. Purification by reverse phase chromatography afforded the title product.

Example 11 Preparation of 5,9-diaza-4,8-dioxo-12-guanidino-dodecanoic acid [compound Id, Where x=3 and n=m=2]

1,3-Dicyclohexylcarbodiimide (490 mg, 2.37 mmol) was added to a solution containing monomethyl succinate (2.16 mmol) and N-hydroxysuccinimide (2.37 mmol) in $CH_2Cl_2$/THF 1:1 (v/v) solution (7 ml). The reaction was left overnight at room temperature. The solution was filtered to remove DCU and washed with dry $CH_2Cl_2$. β-alanine solution in DMF (5 ml) was then added to the active ester solution. After 5 h, the solution was poured into water (100 ml) and the product was extracted with ether. The ether was dried over $Na_2SO_4$ and removed under reduced pressure. The crude coupling product was pure enough for the next step. Coupling with monobenzyloxycarbonyl-propanediamine, deprotection, conversion of the amine to the guanidine and purification was done as in previous examples.

Example 12. Preparation of compound NS-11

N-t-Boc-β-alanine was prepared as described for the N-t-Boc- 6-aminohexanoic acid in Example 1 above and was coupled to a chloromethylated polystyrene 1% divinylbenzene by the cesium salt method. Thus t-Boc-β-alanine (1.73 g, 0.01 mol) was dissolved in water (10 ml) and the pH was adjusted to 7.0 by adding a solution of 1M $Cs_2CO_3$. The solvent was removed under reduced pressure and the residue was dried in vacuo over $P_2O_5$. The dry salt was dissolved in DMF and was added to the polymer. The mixture was kept at 50° C. for 12 h with occasional shaking. The solvent was filtered off and the polymer was washed successively with DMF, DMF:water 9:1 mixture and ethanol and was dried in vacuo. Coupling on the polymer was carried out manually, first with N-t-Boc nipecotic acid (prepared as described for the 6-aminohexanoic acid) followed by N-t-Boc α-aminobutyric acid. All couplings were performed with 3 fold excess of protected amino acid derivatives with an equimolar mixture of N,N'-dicyclohexylcarbodiimide and 1-hydroxybenzotriazole as reagents. Deprotection and cleavage from resin was achieved by treatment with anhydrous HF. The crude product was extracted in 50% acetic acid and lyophilized. Conversion of the amino to the guanidino group was carried out as described above. The final product was purified by reverse phase chromatography followed by preparative HPLC purification.

Example 13. Preparation of compounds NS-8 and NS-15

13.1 Compound NS-8 was prepared on a Merrifield resin (Sigma) starting with N-t-Boc-β-alanine coupled to the polymer as in Example 5. Couplings on the polymer were carried out manually as in Example 5, coupling first to N-t-butyloxycarbonyl pipecolic acid followed by coupling of N-t-butyloxycarbonyl 5-aminovaleric acid. Deprotection, cleavage from the resin and conversion of the amino to the guanidinium group were carried out as in Example 5.

13.2 Compound NS-15 was prepared on a Merrifield resin (Sigma) starting with N-t-Boc-β-alanine coupled to the polymer as in Example 5. Couplings on the polymer were carried out manually as in Example 5, coupling first to N-t-butyloxycarbonyl 3-aminobenzoic acid followed by coupling of N-t-butyloxycarbonyl β-alanine. Deprotection, cleavage from the resin and conversion of the amino to the guanidinium group were carried out as in Example 5.

Figure 2:
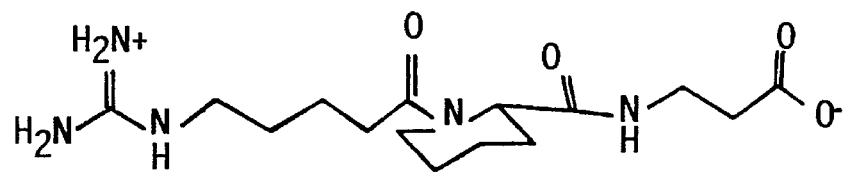
FIG. 2 depicts the chemical structure of compounds according to the invention identified as NS-8, NS-11 and NS-15.
Figure 2:
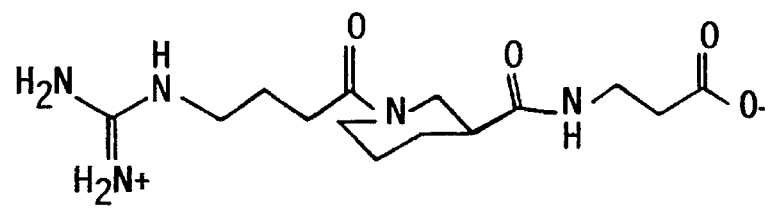
Figure 2:
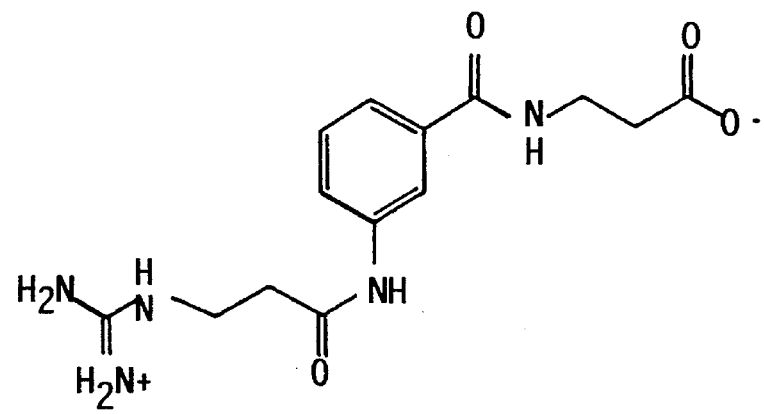

All compounds were characterized by $^1$H-NMR and FAB-MS which were consistent with the assigned structures depicted in FIG. 2.

Example 14. Treatment with trypsin

Compound SF-6,5 and the Gly-Arg-Gly-Asp-Ser (GRGDS; SEQ ID No:15) peptide (50 μg in 100 μl PBS) were incubated at 37° C. and exposed to 0.25% trypsin (Gibco; 50 μl in modified Puck's buffer). Aliquots were taken after 5, 30 and 60 min and monitored by HPLC at 220 nm. Compound SF-6,5 was found intact after 60 min while the GRGDS peptide was completely hydrolized after 5 min.

Example 15. Inhibition of T cell adhesion to ECM protein

To examine the adhesive properties of the T cells, 1 μg/50 μl/well of either fibronectin (FN) (Sigma), the 120 kD cell attachment fragment of FN (Telios Pharm. Inc. San Diego, Calif.), or laminin (LN) (Sigma), were added to 96-flat bottom microtiter-wells for 12 h. Unbound proteins were then washed away and remaining binding sites were blocked with 0.1% bovine serum albumin (BSA) added to the wells for 2 h and washed. CD4+ T cells were purified from peripheral blood mononuclear leukocytes obtained from healthy human donors. The mononuclear cells were isolated using a Ficoll gradient, washed and incubated in RPMI supplemented with 10% fetal calf serum (FCS) and antibiotics in petri dishes at 37° C. humidified $CO_2$ incubator. After 2 h, the non-adherent cells were isolated and applied on nylon-wool columns (1.5 h). $CD4^+$ T cells were then negatively selected by exposure of the cells to a cocktail of anti-CD8, CD19, and CD14 monoclonal antibodies (mAb) conjugated to magnetic-beads (Advanced Magnetics, MA). Unbound cells were recovered and their phenotype was examined. Purity of the $CD4^+$ T cells was always greater than 92% as determined by FACScan.

The purified $CD4^+$ T cells were radioactively labeled with $^{51}$[Cr] (New England Nuclear) in RPMI+20% FCS for 2 h and washed. The cells were counted and seeded ($0.2\times10^5$ cells) on the precoated microtiter wells in the presence or the absence of the various inhibitors. Coating was made either with FN, the 120 kD cell-attachment fragment of FN or with control adhesive protein laminin (LN). The inhibitors were various surrogates according to the invention, other test molecules or mAb. After 30 min incubation (in 37° C. $CO_{2-}$ humidified incubator) the T cells were activated by 10 ng/ml phorbol myristate acetate (PMA) and the percent of T cells attached to the protein substrates was measured. Unbound cells were washed away after 20–30 min, the bound cells were lysed and their radioactivity was measured using radioactive counter. The amount of the radioactivity of the cell lysates represent the matrix-adherent cells and percent binding was calculated in comparison to the total radioactivity added to the wells. Activated T cell adhesion to control wells or to wells coated with BSA was always 2–5%; the level of adhesion of the non-activated T cells was always below 5%. Where indicated, 1/200 diluted mAb anti-CD29 (anti-β1 mAb Serotec, GB), or 1/400 diluted anti-VLA5 (the β1α5 FN-integrin receptor) mAb (Telios Pharm. Inc. San Diego), or 0.2 mM of ARG-Gly-Asp (RGD; SEQ ID No:I), Gly-Arg-Gly-Asp-Ser-Pro-Lys (GRGDSPK; SEQ ID No:16) or Gly-Arg-Gly-Glu-Ser-Pro (GRGESP; SEQ ID No:14) peptides (Sigma) were used. The tested non-peptidic surrogates, 0.2 mM in PBS, were used to pretreat the T cells for 15 min before seeding the cells *, P<0.05. The results shown in Tables 1A, 1B and 1C represent data obtained from several experiments that produced essentially similar results.

In the first series of experiments shown in Table 1A, in which the 120 kD fragment of FN was used, activation of the T cells resulted in cell adhesion to both FN or LN (none). Blocking studies using various mAb to specific integrin sites revealed that T cell binding to both proteins is mediated by β1-VLA integrins: anti-β1 mAb (anti-CD29 mAb) inhibited cell adhesion to both proteins whereas anti-VLA-5 mAb inhibited T cell adhesion to FN but not to LN. T cell adhesion to FN was specifically inhibited by 0.2 mM RGD or GRGDSPK peptides but not by the control peptide GRGESP. The four RGD surrogates, AC-4. AC-14, SF-6,5 and AC-15 inhibited T cell adhesion to FN but not to LN, with a most prominent inhibition exerted by the SF-6,5 surrogate. The ARG-Gly-Glu (RGE; SEQ ID No:7) surrogate SF-6,6 and the amino compound SFN-70 did not inhibit T cell adhesion to both FN and LN.

The inhibitory effect of the RGD analogues on T cell adhesion is not due to a toxic effect since these compounds did not inhibit T cell adhesion to LN nor did they interfere with PMA or a mitogen(phytohemagglutinin)-induced T cell proliferative responses conducted for 48–72 h (data not shown). Thus, the non-peptidic RGD surrogates specifically interfered with T cell adhesion to FN.

TABLE 1A

Specific inhibition of CD4+ T cell Adhesion to FN by RGD Surrogates

| Inhibitor of T cell adhesion | 120 kD fragment of FN | | LN | |
|---|---|---|---|---|
| None | 43 ± 4 | | 55 ± 5 | |
| anti-CD29 mAb | 10 ± 2 * | (83) | 11 ± 2 * | (80) |
| anti-VLA5 mAb | 8 ± 2 * | (82) | 52 ± 4 | (0) |
| RGD | 38 ± 3 | (12) | 57 ± 3 | (0) |
| GRGDSPK | 20 ± 2 * | (54) | 53 ± 4 | (0) |
| GRGESP | 46 ± 3 | (0) | 52 ± 3 | (0) |
| AC-4 | 16 ± 3 * | (47) | 57 ± 4 | (0) |
| AC-14 | 25 ± 4 * | (42) | 55 ± 6 | (0) |
| SF-6,5 | 22 ± 2 * | (49) | 55 ± 6 | (0) |
| AC-15 | 35 ± 5 * | (19) | 52 ± 4 | (0) |
| SF-6,6 | 46 ± 2 | (0) | 52 ± 6 | (0) |
| SFN-70 | 42 ± 5 | (0) | 49 ± 6 | (0) |

In a second series of experiments, FN was used in the adhesion assay carried out with the RGD surrogates NS-8, NS-11 and NS-15 in comparison to ARG-Gly-Asp-Ser (RGDS; SEQ ID No:8) peptide. The results shown in Table 1B indicate that the compound NS-11 is a better inhibitor of cell adhesion than the RGDS peptide.

TABLE 1B

Evaluation of inhibition of CD4+ T cell adhesion to FN by cyclic RGD surrogates

| Inhibitor of T cell adhesion | % Adhesion of activated CD4+ to FN | % Inhibition of adhesion |
|---|---|---|
| None | 65 | — |
| RGDS | 22 | (67) |
| NS-11 | 19 | (71) |
| NS-15 | 27 | (59) |
| NS-8 | 45 | (31) |

In a third series of experiments, FN was used in the adhesion assay with the surrogates SF-6,5 and NS-11 and compared to the peptide Gly-Arg-Gly-Asp-Ser-Pro (GRGDSP; SEQ ID No:13). The results are shown in Table 1C.

TABLE 1C

Inhibition of CD4+ T cell adhesion to FN by RGD surrogates

| Inhibitor of T cell adhesion | Conc. (μg · ml) | % Adhesion of activated CD+ T cell to FN: (% inhibition) |
|---|---|---|
| GRGDSP | 25 | 40 |
| | 50 | 50 |
| | 100 | 75 |
| SF-6,5 | 25 | 10 |
| | 50 | 25 |
| | 100 | 38 |
| | 200 | 55 |
| NS-11 | 25 | 30 |
| | 50 | 50 |
| | 100 | 85 |

Example 16. Inhibition of tumor cell adhesion

To exert their metastatic activity, tumor cells must penetrate blood vessel walls. Since RGD containing peptides have been shown to inhibit metastasis in vivo, it was investigated whether the RGD surrogates of the invention inhibit tumor cell adhesion to the FN and vitronectin (VN) components of the ECM.

To examine the adhesive properties of tumor cells, 1 μg/50 μl/well of FN or 0.3 μg/well of VN were added to 96-flat bottom microtiter wells for 12 h. Unbound proteins were then washed away and remaining binding sites were blocked with 0.1% BSA added to the wells for 2 h and washed. Murine B16-melanoma F-1 cells were metabolically labeled with $^{35}$S-methionine (New England Nuclear) for 2 h, chased for 18 h and extensively washed. The cell suspension was resuspended in RPMI supplemented with 1% BSA containing 1 mM $CaCl_2$ and $MgCl_2$. Tumor cell adhesion to control wells or to wells coated with BSA was always 2–5%. The tested non-peptidic surrogates, 0.2 mM in PBS, were used to pretreat the tumor cells for 15 min before seeding the cells *, P<0.05. The results are shown in Tables 2A and 2B.

In a first series of experiments, the potential inhibitory action of the RGD surrogate SF-6,5 on adhesion of B16 melanoma cells to FN or VN was compared to that of the RGE surrogate SF-6,6 and to that of RGD, GRGDSPK and GRGESP peptides. The results are shown in Table 2A.

TABLE 2A

Inhibition of tumor cells adhesion to FN and VN using RGD surrogates

| Inhibitor of tumor cell adhesion | % Adhesion of B16-melanoma cells to: (% inhibition) | | | |
|---|---|---|---|---|
| | FN | | VN | |
| None | 75 ± 5 | | 68 ± 5 | |
| RGD | 70 ± 3 | (7) | 66 ± 6 | (0) |
| GRGDSPK | 15 ± 4 * | (80) | 10 ± 2 * | (86) |
| GRGESP | 73 ± 5 | (0) | 66 ± 8 | (0) |
| SF-6,5 | 34 ± 4 * | (55) | 40 ± 5 * | (42) |
| SF-6,6 | 75 ± 9 | (0) | 70 ± 7 | (0) |

The B-16 murine melanoma cell adhesion to FN was found to be inhibited by the GRGDSPK peptide, but not by RGD or the RGE peptides, nor by the RGE-surrogate SF-6,6. Nevertheless, the RGD surrogate SF-6,5 inhibited tumor cell adhesion to both FN and VN.

In a second set of experiments carried out in vivo, we were able to clearly demonstrate an inhibition of tumor cell-induced metastases in C57BL/6 mice by i.v. daily administration of 25 μg of compound SF-6,5 per mouse after the induction of metastasis. Both the native peptide GRGDSP and the compound SF-6,6 failed to inhibit metastases.

In a further set of experiments, the inhibitory activity of the RGD surrogates SF-6,5 and NS-11 on the adhesion of B16 murine melanoma cells to FN was compared to that of the GRGDSP peptide. The results are shown in Table 2B.

TABLE 2B

Inhibition of tumor cell adhesion to FN by RGD surrogates

| Inhibitor of tumor cell adhesion | Conc. (μg · ml) | % Adhesion of activated tumor cells to FN: (% inhibition) |
|---|---|---|
| GRGDSP | 25 | 30 |
| | 50 | 40 |
| | 100 | 65 |
| SF-6,5 | 25 | 10 |
| | 50 | 20 |
| | 100 | 30 |
| | 200 | 45 |
| NS-11 | 25 | 35 |
| | 50 | 45 |
| | 100 | 70 |

Example 17. Inhibition of platelet aggregation

To investigate the inhibitory role of the RGD analogues on adhesion, the platelet GPIIb-IIIa receptor which mediates platelet aggregation upon activation was used as a model.

Platelet concentrates were prepared from human whole blood in 10% adenine-citrate-dextrose in Fenwall bags (Baxter Travenol, Israel) followed by standard AABB protocol. Platelet rich plasma was prepared by centrifugation (2500 rpm for 5 min). Samples of platelets were counted in a Minos AST Cell Counter (Levoiselle, France). Cell aggregation was induced by 5 mM ADP and monitored at 695 mm in a 4-channel Aggregometer (Bio-Data, Hatboro, Pa.). To evaluate the effect of the various RGD peptides and the peptide analogues, the platelet rich plasma was pre-incubated with the various inhibitors for 10 min at 37° C. with 10 μl solutions followed by the induction of aggregation.

Figure 3:
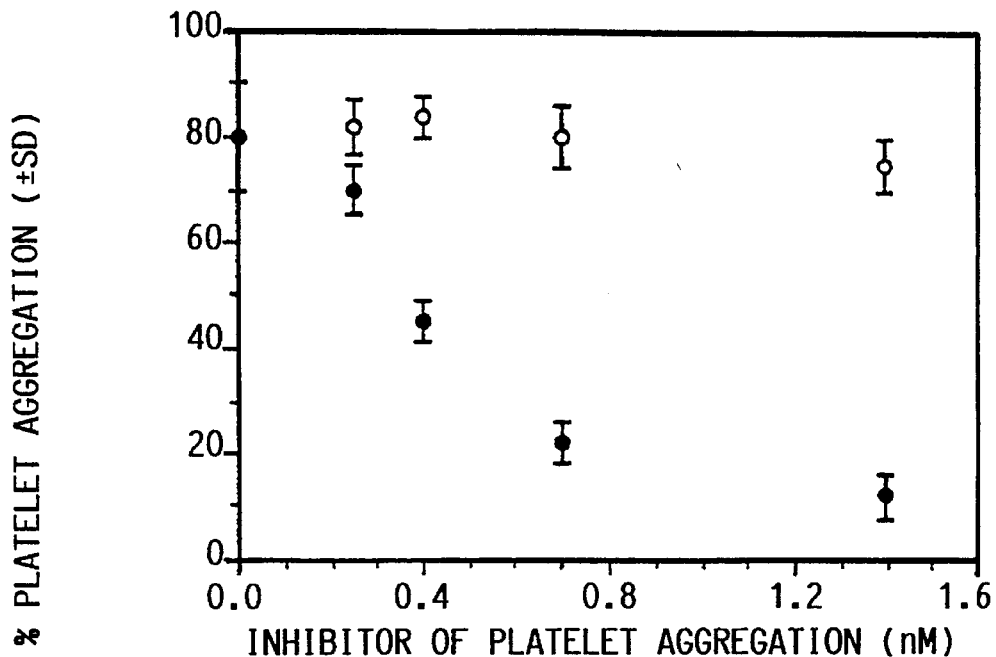
FIG. 3 shows a dose-dependent curve of inhibition of platelet aggregation by compounds SF-6,5 (filled circles) and SF-6,6 (empty circles).

FIG. 3 shows a dose-dependent curve of inhibition of platelet aggregation by the compounds SF-6,5 (filled circles) and SF-6,6 (empty circles). Compound SF-6,5, but not SF-6,6, was found to inhibit the aggregation of platelet rich plasma in a dose-dependent fashion with $IC_{50}$ of 0.3 mM.

Figure 4:
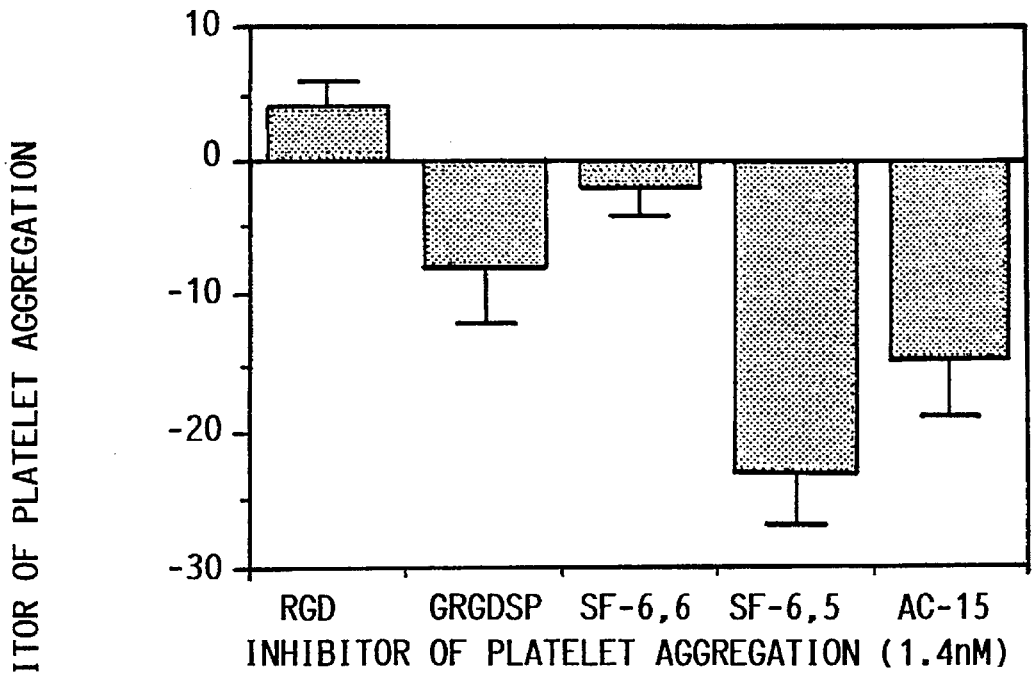
FIG. 4 illustrates inhibition of platelet aggregation by the compounds of the invention SF-6,5 and AC-15, and the compounds RGD, Gly-Arg-Gly-Asp-Ser-Pro (GRGDSP; SEQ ID No:13) and SF-6,6 for comparison.

To examine the specificity of the inhibitory effect of the RGD-analogues on platelet aggregation, the cells were treated with various peptidic (RGD and GRGDSP) and nonpeptidic (SF-6,6, SF-6,5 and AC-15) RGD analogues used at a fixed sub-saturating concentration of 0.5 mM. FIG. 4 shows inhibition of platelet aggregation using 10 μg/ml concentration of the inhibitors (the results shown here summarizes the data obtained from a total of 4 experiments). These results show that the tripeptide RGD itself was not an effective inhibitor while the larger peptide GRGDSPK exerted a marked inhibitory effect on platelet aggregation. In addition, the inhibitory effect of the RGD surrogates SF-6,5 and AC-15 was even higher than that of the GRGDSPK peptide. The control surrogate, compound SF-6,6, had a very limited inhibitory effect on platelet aggregation reflecting the inability of RGE to inhibit platelet aggregation.

Example 18. Inhibition of platelet aggregation by NS-11

An in vitro assay as described in Example 17 was carried out with the compound NS-11 to examine its ability to interfere with platelet aggregation, and compared it to the SF-6,5 surrogate.

Table 3 summarizes the results obtained in analyzing the effect of both molecules on the ADP-induced platelet aggregation.

TABLE 3

NS-11 mediated inhibition of platelet aggregation

| Compound | Concentration | Percent inhibition of aggregation |
|---|---|---|
| GRGDSP | 0.1 mM | 75 |
| SF-6,5 | 0.1 mM | 25 |
| | 0.3 mM | 55 |
| NS-11 | 0.1 mM | 90 |
| | 0.3 mM | 100 |

It can be summarized that the three compounds tested were found to induce inhibition of platelet aggregation. The surrogate SF-6,5 had a mild, though significant effect on aggregation: comparing its effect to that of the RGD-containing peptide on a mM basis, reveals that this molecule had slightly lower effect on the cell function. The results obtained indicate that NS-11 is a better inhibitor of platelet aggregation than SF-6,5. Moreover, this molecule is a significantly better inhibitor than the RGD-containing peptide. Its effect at the concentration of 0.1 mM is better than that of the RGD-peptide, used at the same concentration, by almost 20%.

Example 19. Inhibition of platelet aggregation by NS-8, NS-11, and NS-15

Figure 5:
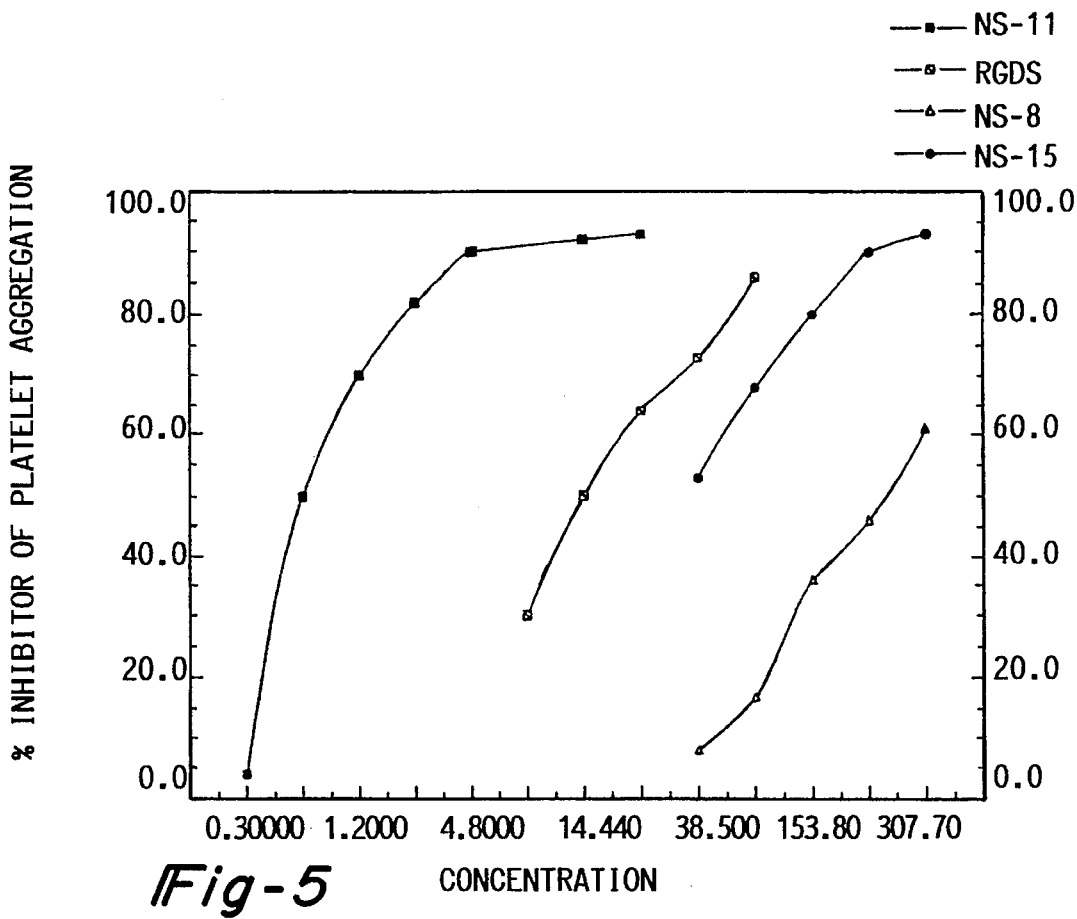
FIG. 5 illustrates platelet aggregation inhibition by the compounds of the invention NS-8 (empty triangles)i, NS-11 (filled squares) and NS-15 (filled circles) in comparison to peptide ARG-Gly-Asp-Ser (RGDS; SEQ ID No:8) (crossed squares).

Platelet rich plasma (PRP) was prepared from acid/citrate/dextrose anti-coagulated fresh human blood by differential centrifugation. Platelet aggregation was induced by 5 mM ADP and monitored at 695 nm by a 4-channel Aggregometer (Bio-Data, PA). To evaluate the effect of the RGDS peptide and the. NS-8, NS-11 and NS-15 analogs, the PRP was preincubated with the inhibitors for 10 minutes at 37° C., prior to the induction of aggregation. As seen in FIG. 5, compound NS-11 was a better inhibitor of platelet aggregation than either NS-8 and NS-15. Moreover, compound NS-11 was found to inhibit platelet aggregation better than the RGD-containing peptide (RGDS). In fact, 50% inhibition of platelet aggregation was achieved using a 30-fold lower concentration of NS-11 than that of RGDS.

Example 20. Inhibition of the binding capacity of anti-GPIIb-IIIa mAb (PAC-1) to platelets To investigate whether the RGD surrogates actually bind to the GPIIb-IIIa integrin, their ability to compete with a monoclonal antibody (mAb) specific to GPIIb-IIIa was investigated. This mAb, designated PAC-1, specific for the activated receptor, binds GPIIb-IIIa in an RGD-dependent manner (Taub, R. et al. (1989) J.Biol.Chem. 264: 259).

Figure 6:
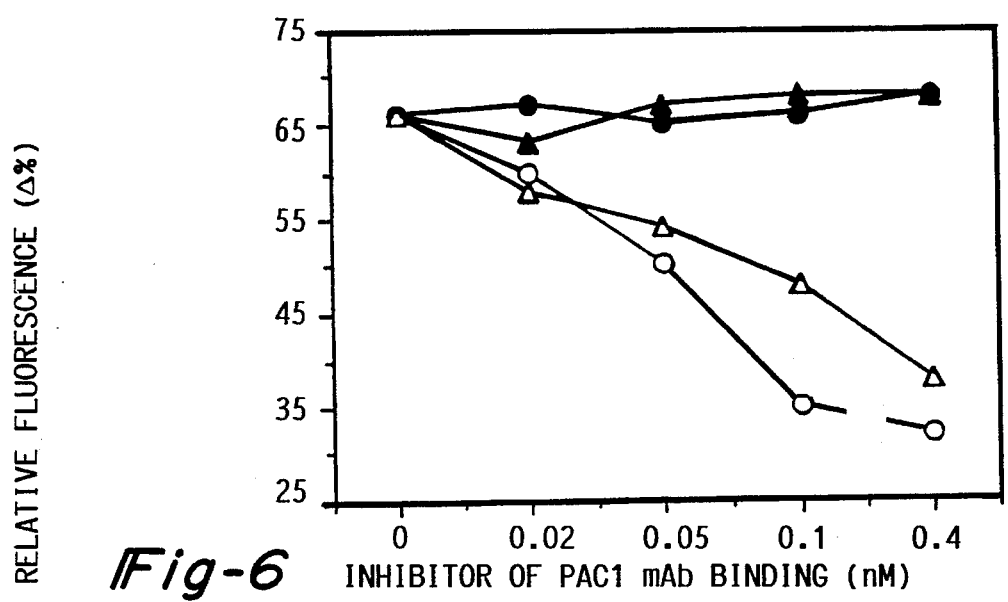
FIG. 6 illustrates inhibition of the binding capacity of anti-GPIIb-IIIa monoclonal antibody (PAC-1) to platelets by the compound of the invention SF-6,5 (empty triangles), in comparison to compound SF-6,6 (filled circles) and peptides GRGDSPK (empty circles) and Gly-Arg-Gly-Glu-Ser-Pro (GRGESP; SEQ ID No:14) (filled triangles).

ADP-activated platelets were incubated with FITC-conjugated PAC-1 mAb in the presence of various peptidic and non-peptidic compounds, as follows: the platelet rich plasma were gel-filtrated into modified Tryode's solution (137.5 mM Nacl, 4 mN Hepes, 2.6 mM KCl, 1 mM $MgCl_2$, 3.3 mM $NaH_2PO_4$, 5.6 mM glucose at pH 7.4) containing 350 µg/ml BSA (which was used as the incubation buffer in further steps; Tryode's/BSA). The final count in the cell assays was $2 \times 10^6$ per ml. The cells were then activated with 10 µM ADP and epinephrine. To examine RGD peptides and related analogues as competitors for the binding capacity of the PAC-1 mAb to platelets, the cells were incubated in 50 µl Tryode's/BSA supplemented with 1 mM $CaCl_2$ for 30 min in 25° C., in the presence of 0–500 µM peptides or peptide-analogues with 10 µg/ml FITC labeled PAC-1. The fluorescence profile of the cells was determined using FACScan (Beckton Dickenson) at 488 nm. In FIG. 6: GRGDSPK (empty circles), GRGESP (filled triangles), compound SF-6,5 (empty triangles), compound SF-6,6 (filled circles) (the data shown here represent results obtained in one of three experiments which were essentially identical).

The results shown in FIG. 6 indicate that both the RGE peptide and the RGE analogue compound SF-6,6 failed to inhibit PAC-1 binding to the platelet integrin receptor. However, the GRGDSPK and the RGD surrogate, compound SF-6,5, inhibited PAC-1 staining of the cells in a dose-dependent manner. Thus, the ability of the RGD surrogate compound to inhibit platelet aggregation could be attributed to direct interference with the RGD binding site on the GPIIb-IIIa receptor.

Example 21. Inhibition of DTH response to OX by treatment of mice with RGD surrogate To examine the regulatory role of SF-6,5 on T cell immunity and lymphocyte migration in vivo, a delayed-type hypersensitivity (DTH) reaction experiment was performed in which groups of BALB/c mice (6 mice per group) were sensitized on the shaved abdomen with the skin allergen 4-ethoxymethylene- 2-phenyl oxazolone (OX) (10 µl of 3% OX in acetone/olive oil) and challenged again 5 days later by applying OX to their ears. The increment in ear swelling was recorded 24 hours later as a measure of DTH. The individual measuring of ear swelling was blinded to the identity of the groups of mice. GRGDS, RGD surrogate compound SF-6,5 and RGE surrogate compound SF-6,6 were administered I.V. in 200 µl PBS into the tail vein on the indicated days. Control groups of mice were treated identically with PBS.

The results shown in Table 4 indicate that treatment with compound SF-6,5 but not with SF-6,6, inhibited the DTH response best when the mice were injected for 6 days (groups 7 and 8, respectively). In addition, the RGD surrogate was found to be a better inhibitor of the DTH response than the GRGDS peptide, most probably due to shorter physiological retention-times of the latter (group 3). Indeed, as shown in Example 14, it was found that the compound SF-6,5, unlike the GRGDS peptide, was completely resistant to trypsin-induced hydrolysis. The results obtained in these groups did not differ significantly from those obtained in the positive control group (data not shown),*: $P<0.01$; P values were measured in relation to group 2, the positive control group. These findings indicate that modulation of cell-mediated immune reactions in vivo may be achieved by relatively low doses of non-peptidic RGD analogue, most probably by means of interfering with lymphocyte migration.

TABLE 4

Inhibition of DTH response to OX by treatment of mice with RGD surrogate

| | Treatment of mice | | Elicitation of OX-mediated DTH response | | |
|---|---|---|---|---|---|
| Group | Compound: | injected on days: | OX-sensitization | Δ Ear swelling ($\times 10^{-2}$ mm ± SD) | % inhibition |
| 1 | None | — | No | 2 ± 2 | — |
| 2 | None | — | Yes | 21 ± 2 | — |
| 3 | GRGDSPK | 1 to 6 | Yes | 17 ± 3 | 20 |
| 4 | SF-6,5 | 1 | Yes | 16 ± 3 | 20 |
| 5 | | 1, 3 | Yes | 13 ± 2 | 34 |
| 6 | | 1, 3, 5 | Yes | 8 ± 2 * | 62 |
| 7 | | 1 to 6 | Yes | 2 ± 1 * | 95 |
| 8 | SF-6,6 | 1 to 6 | Yes | 23 ± 4 | None |

REFERENCES

Adler, M., Lazarus, A., Dennis, M. S. & Wagner, G. (1991) Science 253:445–447.

Alon, R. et al., (1990) BBRC 170:1236–1241.

Barany, N. & Merrifield, R. B. The Peptides. Analysis, Synthesis and Biology (Gross, E. Ed.) Academic Press, New York, 1980, p. 2.

D'Souza, S. E., Ginsberg. M. H., Matsueda, G. R. & Plow, E. F. (1991a) Nature 350: 66–68.

D'Souza, S. E. et al. (1991b) TIBS 16:246.

Elices, M. J., Urry, A. & Hemler, M. E. (1991) J. Cell Biol. 112:169–181.

Humphries, M. J., Olden, K. & Yamada, K. M. (1986) Science 233:467–470.

Hynes, R. O. (1990) Fibronectins, Sperger, Verlag.

Hynes, R. O. (1992) Cell 69:11–25.

Mazerolles, F. et al. (1988) Cell 55:497–504.

Mazerolles, F., Amblard, F., Lumbroso, C., Lecomte, O., Van de Moortele, P. F., Barbat, C., Piatier-Tonneau, D. & Fisher, A. (1990) Eur. J. Immunol. 20:637–644.

Mould, A. P. et al. (1991) J. Biol. Chem. 266:3579–3585.

Ouaissi, M. A., Cornette, J., Afchain, D., Capron, A., Gras-Masse, H. and Tartar, A. (1986) Science 234:603–607.

Philips, D. R., Charo, I. F. & Scarborough, R. M. (1991) Cell 65:359–362.

Ruoslahti, E. (1988) Annu. Rev. Biochem. 57:375–391.

Ruoslahti, E. & Giancotti, F. G. (1989) Cancer Cell 1:119–126.

Ruoslahti, E. et al. (1989) Cancer Cells 111:249.

Ruoslahti, E. (1991) J. Clin. Invest. 87:1–5.

Shimizu, Y., van Seventer, G. A., Horgan, K. J. & Shaw, S. (1990) Nature 345:250–253.

Shimizu, Y. & Shaw, S. (1991) FASEB J. 5:2292–2299.

Springer, T. A. (1990) Nature 346:425–434.

Taub, R., Gould, R. J., Garsky, V. M., Ciccarone, T. M., Hoxie, J., Friedman, P. A. & Shattill, S. J. (1989) J. Biol. Chem. 264:259–265.

Van Seventer, G. A. et al. (1991) Curr. Opin. Immunol. 3:294.

Vogel, B. E. et al (1992) J. Cellular Biochem. 16F:154.

Yamada, K. M. & Kennedy, D. W. (1984) J. Cell Biol. 99:29–36.

Yamada, K. M. & Kennedy, D. W. (1987) J. Cell Physiol. 130:21–28.

We claim:

1. A method of inhibition of cell adhesion dependent on cell-adhesion-motif ARG-GLY-ASP (RGD; SEQ ID No:1) interactions which comprises administering a compound of the formula I $$H_2N-C(=NH)-NH-CH_2-A-CH_2-CO_2H \quad (I)$$

and pharmaceutically acceptable salts thereof, wherein A is a chain of 9 atoms selected from the group consisting of:

$-(CH_2)_n-CO-NH-(CH_2)_{7-n};$ (i)

$-(CH_2)_n-NH-CO-(CH_2)_{7-n};$ (ii)

$-(CH_2)_x-CO-NH-(CH_2)_n-CO-NH-(CH_2)_m;$ (iii)

$-(CH_2)_x-NH-CO-(CH_2)_n-NH-CO-(CH_2)_m;$ (iv)

(v)

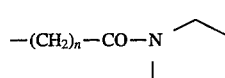

and

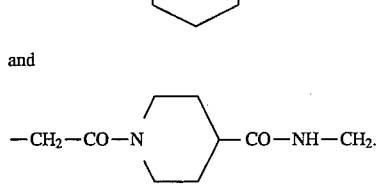

(vii)

wherein each of x, n and m is at least 1; in chains (i) and (ii) n is at most 6; in chains (iii) and (iv) the sum of x+n+m is 5; and the sum of n+m is 4 in chain (v) and 3 in chain (vi).

2. The method according to claim 1, wherein the compound has the formula

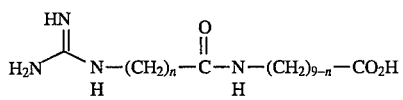

(Ia)

wherein n is at least 1 and at most 8.

3. The method according to claim 1, wherein the compound has the formula

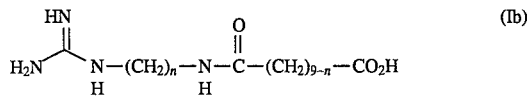

(Ib)

wherein n is at least 1 and at most 8.

4. The method according to claim 1, wherein the compound has the formula

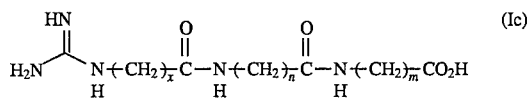

(Ic)

wherein each of x, n and m is at least 1 and the sum of x+n+m is 7.

5. The method according to claim 1, wherein the compound has the formula

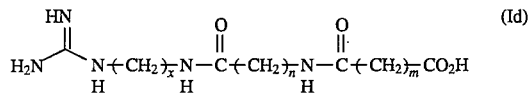

(Id)

wherein each of x, n and m is at least 1 and the sum of x+m+n is 7.

6. The method according to claim 1, wherein the compound has the formula

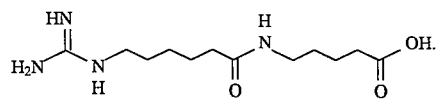

7. The method according to claim 1, wherein the compound has the formula

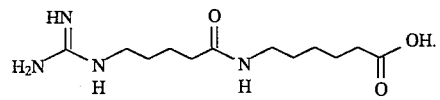

8. The method according to claim 1, wherein the compound has the formula
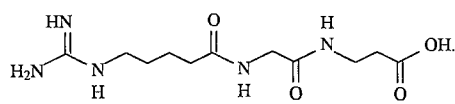
9. The method according to claim 1, wherein the compound has the formula
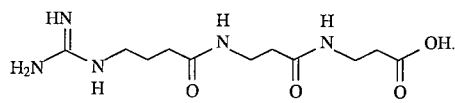
10. The method according to claim 1, wherein the compound has the formula
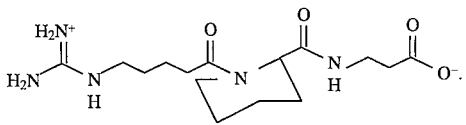
11. The method according to claim 1, wherein the compound has the formula
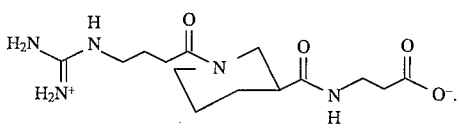
* * * * *